United States Patent
Phillips et al.

[19]

[11] Patent Number: 5,857,685

[45] Date of Patent: Jan. 12, 1999

[54] SUPPORT CART APPARATUS FOR SUPPORTING INTRAVENOUS FLUID DISPENSING SYSTEMS

[76] Inventors: James R. Phillips; Janice F. Phillips, both of 458 Rocky Point, Cordova, Tenn. 38018

[21] Appl. No.: 513,131

[22] Filed: Aug. 9, 1995

[51] Int. Cl.$^6$ .................................................. B62B 3/02
[52] U.S. Cl. .................. 280/47.35; 248/129; 312/249.8; 312/249.13
[58] Field of Search ............................. 280/47.34, 47.35; 248/125.8, 129, 121, 122.1, 125.1, 145.6; 312/249.8, 249.11, 249.12, 249.13; 604/80, 246

[56] References Cited

U.S. PATENT DOCUMENTS

| | | | |
|---|---|---|---|
| 1,097,163 | 5/1914 | Brown | 280/47.35 |
| 3,709,556 | 1/1973 | Allard et al. | 248/125.1 |
| 3,933,275 | 1/1976 | Metzner et al. | 248/129 |
| 4,542,909 | 9/1985 | Littwin et al. | 280/79.11 |
| 4,678,460 | 7/1987 | Rosner | 604/80 |
| 4,691,397 | 9/1987 | Netzer | 280/30 |
| 4,832,294 | 5/1989 | Eidem | 248/123 |
| 5,000,407 | 3/1991 | Judi et al. | 248/125 |
| 5,110,076 | 5/1992 | Snyder | 248/125 |
| 5,112,019 | 5/1992 | Metzler et al. | 248/405 |
| 5,114,023 | 5/1992 | Lavin | 211/107 |
| 5,135,191 | 8/1992 | Schmuhl | 248/125 |
| 5,292,094 | 3/1994 | Vankuiken | 248/125 |
| 5,319,816 | 6/1994 | Ruehl | 248/121 |
| 5,337,992 | 8/1994 | Pryor et al. | 248/125.1 |
| 5,344,169 | 9/1994 | Pryor et al. | 280/47.35 |
| 5,479,953 | 1/1996 | Pasulka | 248/129 |
| 5,492,537 | 2/1996 | Vancaillie | 604/246 |
| 5,518,310 | 5/1996 | Ellman et al. | 312/249.12 |
| 5,524,916 | 6/1996 | Redens | 280/32.6 |
| 5,542,635 | 8/1996 | Smith et al. | 280/47.35 |
| 5,556,065 | 9/1996 | Wadley | 248/129 |

*Primary Examiner*—Brian L. Johnson
*Assistant Examiner*—Min Yu
*Attorney, Agent, or Firm*—Garvey, Smith, Nehrbass & Doody, L.L.C.

[57] ABSTRACT

A hospital support cart for supporting intravenous fluid dispensing systems includes a rectangular frame having a lower base with multiple corners and an upper table with a work surface thereon spaced above the base, the base and the work surface provide generally rectangular periphery. The work surface table provides X and Y axes that intersect at the center of the table work surface and which respectively bisect two parallel sides of the work surface. Each of the axes is parallel to two sides of the table work surface. A plurality of telescoping fluid container support poles are supported by the frame each being vertically oriented and including at least two poles being placed on opposite sides of the Y axis and at least one pole that is placed on one side of the X axis. The frame is preferably wheeled so that the apparatus can be moved about a hospital room or the like.

1 Claim, 3 Drawing Sheets

SUPPORT CART APPARATUS FOR SUPPORTING INTRAVENOUS FLUID DISPENSING SYSTEMS

BACKGROUND OF THE INVENTION

1. Field of the Invention

The present invention relates to hospital cart devices and more particularly an improved hospital cart for supporting intravenous fluid dispensing systems (for example bottle, IV tube, and needle assembly), wherein a frame having upper and lower spaced apart rectangular plates supports a plurality of outer tubes arranged in a generally triangular pattern, each of the tubes having an inner telescoping portion that can be elevated to a desired level. Two of the telescoping poles are positioned on the same side of an X axis of the frame and the other pole is positioned on the opposite side of the X axis. One of the poles lies on the Y axis of the frame while the other two poles are on opposite sides of the Y axis of the frame. This triangular relationship affords improved stability to the cart which is preferably wheeled.

2. General Background

Hospitals employ various support structures for supporting an intravenous (IV) fluid dispensing system adjacent the patient that receives fluid from the dispensing systems such as blood, saline, medications and the like. One of the most common supports for IV fluid systems is a telescoping pole having hooks at the top of the pole to which the fluid containing a bag or bottle is attached. These poles can telescope to position on IV bottle 6–8 ft. in the air. They typically provide a multi-legged base having radially extending feet that are spaced circumferentially about the bottom of the pole. Commercially available IV poles are usually wheeled so that the patient can move freely about his or her room and rolling the IV support pole and the IV fluids system with the pole.

One of the notorious problems associated with such IV support poles is their instability. These devices are typically very tall and have a relatively small diameter base. They can easily topple over especially when the patient is sedated or weak from surgery.

Some IV poles are mounted directly to the patient's bed, and can be elevated to a desired height and then set with a set screw or pin at a desired elevation. However, these poles are of no value to the patient that is able to move about the room because they necessarily restrict the patient and the IV fluid's delivery system to the bed and its immediate area.

Several devices have been patented which proport carry IV fluids delivery systems and allow mobility to the patient that is receiving such fluids.

A motorized IV pole assembly is the subject of U.S. Pat. No. 5,112,019 in that patent, a motorized IV pole system for controlling the height of an IV container to thereby control the infusion pressure in an IV tube includes a telescoping IV pole system. In one embodiment, comprising three concentric support members, the outer support member is fixed, the middle support member is reciprocable with respect to the outer support member and is driven by a rack gear attached thereto. An inner support member is reciprocatable in the interior of the middle support member and is driven by a cable attached to the outer support member passing over a pulley attached to the middle support member. The rack on the middle support member may be driven by a shaft to which is attached a hand crank and AC motor. The AC motor may be driven by a programmable control system which includes an optical encoder to permit display of the height of the IV container. Also, preselected heights and various speeds of height adjustment may be utilized. Another embodiment employs a tubular support member carrying a nut driven by a concentric threaded shaft. A friction-adjustable bearing for maintaining the position of the shaft permits manual height adjustment.

In U.S. Pat. No. 5,110,076, an improved adjustable multiple support stand is provided wherein each of a plurality of support poles is individually adjustable to a desired height. The stand generally comprises a plurality of vertically oriented support poles mounted in a parallel array about an upright main or center post and adapted for vertical sliding movement between raised and lowered positions. Spring loaded trigger assemblies carried by the support poles include locking pins registrable with vertically spaced notches in the center post to permit individual height adjustment of each support pole. The uppermost end of each support pole includes a hook or is otherwise suitably adapted to support a medical fluid container such as a bag of intravenous fluid or the like.

A portable IV stand is the subject of U.S. Pat. No. 4,832,294 issued to John Eidem. The Eidem patent discloses a portable stand that is provided for the transport of infusion pumps, intravenous solutions and other associated equipment. The stand consists of a T-shaped base having a base member with a base leg extending perpendicularly therefrom. Large, diameter non-swiveling wheels are located at either end of the base member and the caster wheel is located at the end of the base leg. A skid member is provided to assist in the transport of the stand on stairs. A cylinder support platform may be affixed to the T-shaped base.

The Schmuhl U.S. Pat. No. 5,135,191 discloses a medical support system that comprises a pole for supporting intravenous related medical equipment. The pole has two different diameters to enable it to be interchangeably inserted into a wheeled strand, a wheelchair bracket, and a gurney cart socket. A stop in the stand limits insertion of the pole into the stand, and a locking knob locks the pole to the stand. The pole and the stand are designed to enable the pole to be inserted into and withdrawn from the stand under normal ceilings without having to tip the stand. The wheelchair bracket receives and locks the pole in a manner similar to the stand. The medical support system enables a patient connected to the intravenous related medical equipment to be transported in a wheelchair or gurney cart without also having to transport the stand.

A bracket for attachment of IV stand to a hospital transport device is disclosed is U.S. Pat. No. 5,292,094. The apparatus includes a bracket such that an IV stand may be quickly connected to a wagon. In this fashion, the IV stand and a wagon can move as the unit for transport of patients. The bracket insures that the IV stand is held closely to the wagon such that it requires relatively lateral space and such that it is guided against lateral tipping.

In the Lavin U.S. Pat. No. 5,114,023 a utility tray is disclosed for supporting medical paraphernalia and guiding hollow tubing which is adapted for mounting to an upstanding vertical pole used for supporting intravenous solution containers. The tray has a plurality of varying diameter circular openings for enforcing and supporting cylindrical objects. A clamp along one edge of the tray is used to attach the tray to the upstanding vertical pole. Slots cut along an edge of the tray have a gradually diminishing width to receive hollow tubing. By pushing the tubing into the slot, the flow of fluids through the tubing is stopped. Tube guides also cut along the perimeter edge of the tray are used to keep several tubes from becoming intertwined.

U.S. Pat. No. 5,000,407 discloses a switch bag type blood-gathering set used for transfusing blood gathered from a blood donor to the same blood donor again, and for newly gathering predetermined amount of blood from the blood donor. This switch bag type blood-gathering set comprises a liquid transferring member for introducing a physiological saline solution into the blood-gathering set, a blood transfusing member for introducing blood from a blood bag into the blood-gathering set, a blood-transfusing and gathering member for supplying blood to or gathering blood from the donor, a washing solution storing member for containing a waste liquor after priming in the blood-gathering set, and a blood storing member for storing blood gathered from the donor, and these constituents are connected by connecting tubes so as to not contact with the air outside.

SUMMARY OF THE INVENTION

The present invention provides an improved support cart apparatus for use in supporting intravenous fluid dispensing articles such as for example an IV bottle or bag, delivery tubes, and IV needles attached to the patient.

The present invention provides an improved cart apparatus that has a rectangular frame having a lower base and an upper table with a work surface thereon spaced above the base. The work surface provides a generally rectangular periphery and the table has "X", and "Y" axes that intersect at the center of the table work surface and the axes respectively intersecting parallel sides of the work surface.

A plurality of intravenous fluid container support poles are mounted to the frame, each being telescoping to adjust to multiple elevational positions. Each of the support poles include a lower outer tube portion and an upper inner tube portion that telescopes within the outer tube portion. At least two of the poles are supported on one side of the X axis of the work surface and the other pole is placed on the other side of the X axis of the work surface. Further, at least two of the poles are placed on opposite sides of the Y axis of the table work surface.

A plurality of casters are mounted at corners of the lower base portion of the frame.

In the preferred embodiment, the base and work surface portions are each rectangular, and the plurality of casters are positioned respectively at the corners of the base, preferably including at least two fixed casters and two swiveling casters.

In the preferred embodiment, a lever activated brake assembly locks the rear casters to prevent movement of the apparatus.

In the preferred embodiment, the upper table portion comprises a fixed table portion and a foldable table portion attached thereto, the foldable table portion being extendable from the upper table surface and substantially parallel thereto. In the preferred embodiment, an electrical supply comprising a plurality of receptacles, communicates with the frame and includes a cord for supply of electrical power to the frame adjacent the upper work surface.

In the preferred embodiment, a handle extends substantially the dimension of at least one side of the cart.

In the preferred embodiment, the poles are positioned in a triangular pattern with reference to the upper work surface.

In the preferred embodiment, each of the poles include an outer pole that extends a short distance above the table work surface and an inner pole that telescopes within the outer pole and further comprising clamps for affixing the inner pole to the outer pole.

In the preferred embodiment, a flexible skirt extends downwardly from the base to a position adjacent the bottom of the casters for preventing entanglement of objects with the casters during use.

BRIEF DESCRIPTION OF THE DRAWINGS

For a further understanding of the nature and objects of the present invention, reference should be had to the following detailed description, taken in conjunction with the accompanying drawings, in which like parts are given like reference numerals, and wherein.

DETAILED DESCRIPTION OF THE PREFERRED EMBODIMENT

Figure 1:
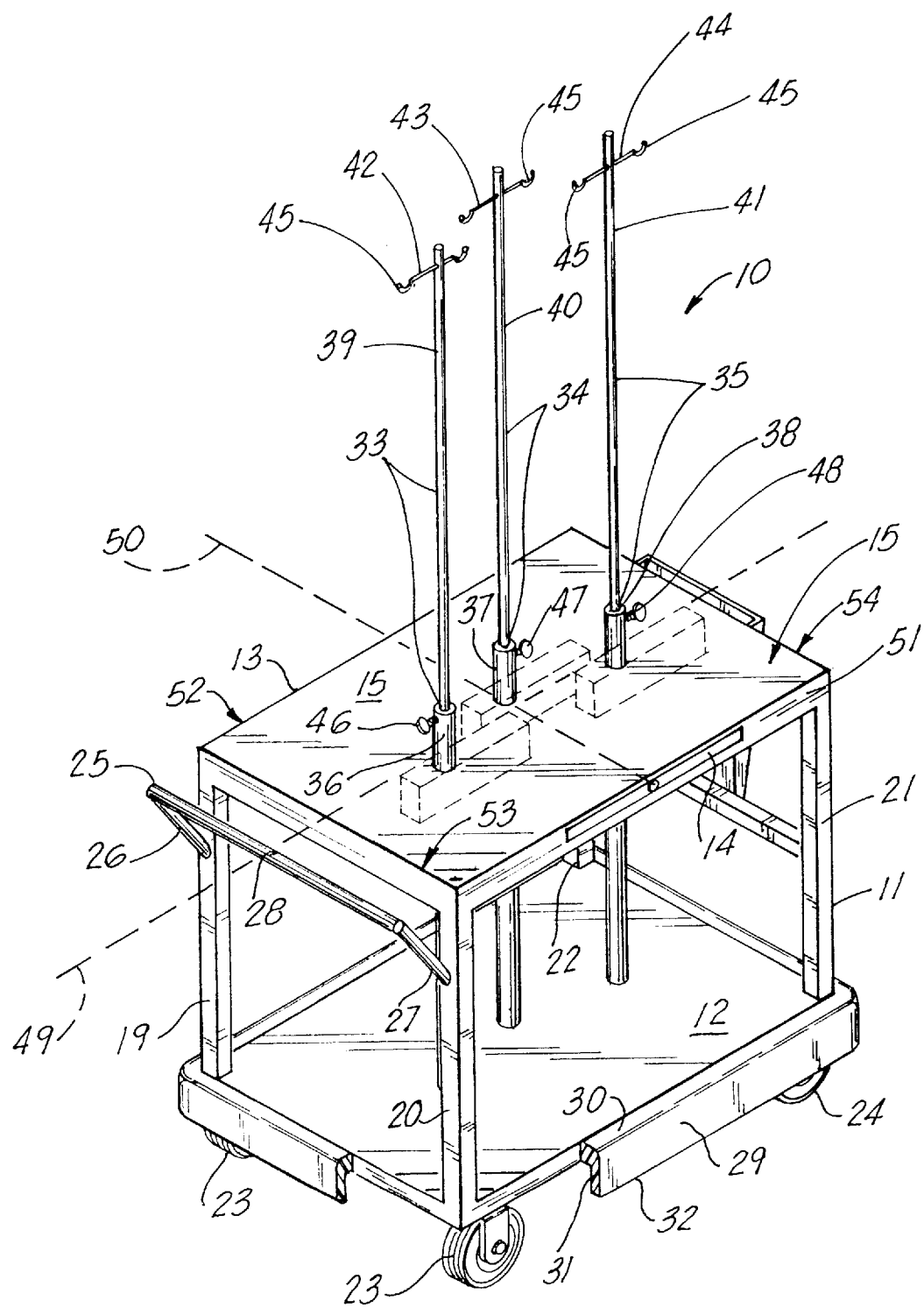
FIG. 1 is perspective view of the preferred embodiment of the apparatus of the present invention.

FIGS. 1 and 3–5 show the preferred embodiment of the apparatus of the present invention designated generally by the numeral 10. Fluid support cart 10 has a support frame 11 that includes a generally rectangular bottom plate 12 and a corresponding generally rectangular top plate 13 having a rectangular upper work surface thereon.

Figure 3:
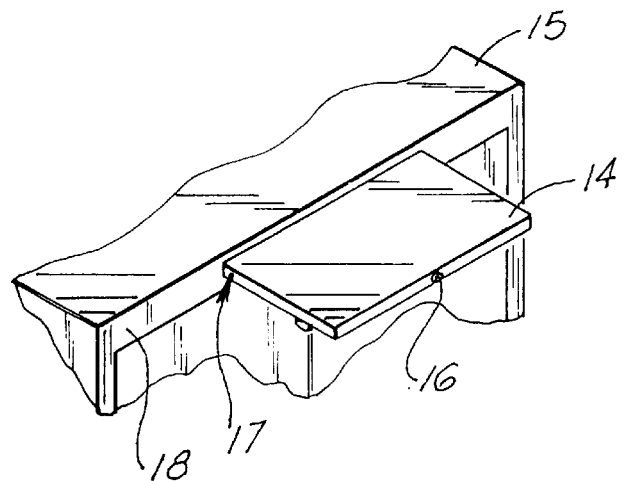
FIG. 3 is a fragmentary view of the preferred embodiment of the apparatus of the present invention.

A movable, retractable storage shelf 14 is slidably mounted in relation to work surface 15. Shelf 14 can be movable upon rails (not shown) so that the shelf 14 can be pulled to an extended position as shown in FIG. 3 or pushed to a retractive position as shown in FIG. 1 relative to work surface 15.

Frame 11 includes a front panel 18 having a rectangular opening 17 for receiving storage shelf 14. Knob 16 on the front of shelf 14 can be used to manipulate the storage shelf 14 between the extended position of FIG. 3 and the retractive position of FIG. 1.

Frame 11 further includes a plurality of vertical posts 19–22 that extend from corners of bottom plate 12 to corners of top plate 13 as shown in FIG. 1. Casters 23 are positioned at the corners of bottom plate 12 immediately beneath each of the posts 19–22. In the preferred embodiment, two of the casters 23 are swiveling casters and two of the casters 23 are fixed. The casters 23 are preferably swiveling casters and the casters 24 are preferably fixed.

Handle 25 extends from post 19 to post 20. Handle 25 includes a pair of diagonally extending members 26, 27 that are mounted respectively to the upper end portion of posts 19, 20. Handle 25 further comprises a horizontal section 28 that is at an elevation about equal to the elevation of the table work surface 15.

A flexible skirt 29 extends around bottom plate 12 as shown in FIG. 1. Skirt 29 includes a horizontal section 30 that affixes to the periphery of bottom plate 12 and a vertical section 31 that is integral with horizontal section 30 and which provides a lower edge 32 that extends downwardly to an elevation that is near the bottom of casters 23, 24. The edge 32 can for example be a few millimeters from the bottom of casters 23, 24. Skirt 29 prevents an entanglement of objects such as mops, electrical cords, a user's foot and the like with casters 23, 24, forming a guard about frame 11 at its lower end portion adjacent bottom plate 12 as shown.

A plurality of telescoping poles 33, 35 are provided, each rigidly affixed to the frame 11 as shown in FIG. 1. Each telescoping pole 33–35 includes an outer tube 36–38 respectively that is hollow providing a vertical open ended bore for receiving an inner pole 39, 41 respectively as shown in FIG. 1. Each of the poles 39, 41 provides an upper hanger 42, 44 respectively. Each of the hangers provides two opposed hooks 45, either of which can support a container of IV fluids such as for example a bottle, plastic bag, or the like.

A plurality of set screws 46–48 are threadably attached to the upper end of each of the outer tubes 36–38. The user can affix a selected hole 39, 41 in a desired elevational position by tightening the selected set screw 46–48.

Each of the outer tubes 36–38 is rigidly affixed to frame 11, being attached to bottom plate 12 by welding for example and by extending through circular openings in work surface 15. Outer tubes 36–38 are rigidly attached to upper plate 13 by welding for example.

The table work surface 15 is generally rectangular, and in FIG. 1 is centrally intersected by "X" axis 49 and by "y" axis 50. The X axis 49 is generally parallel to upper plate 13 sides 51, 52. Similarly, the Y axis 50 is generally parallel to upper plate 13 sides 53, 54. A pair of the telescoping poles 33, 35 are positioned on the opposite sides of the Y axis 50. A single one of the poles 34 is positioned on one side of the X axis 49. Thus, the poles 33, 35 are positioned in a generally triangular pattern as shown in the drawings.

Figure 2:
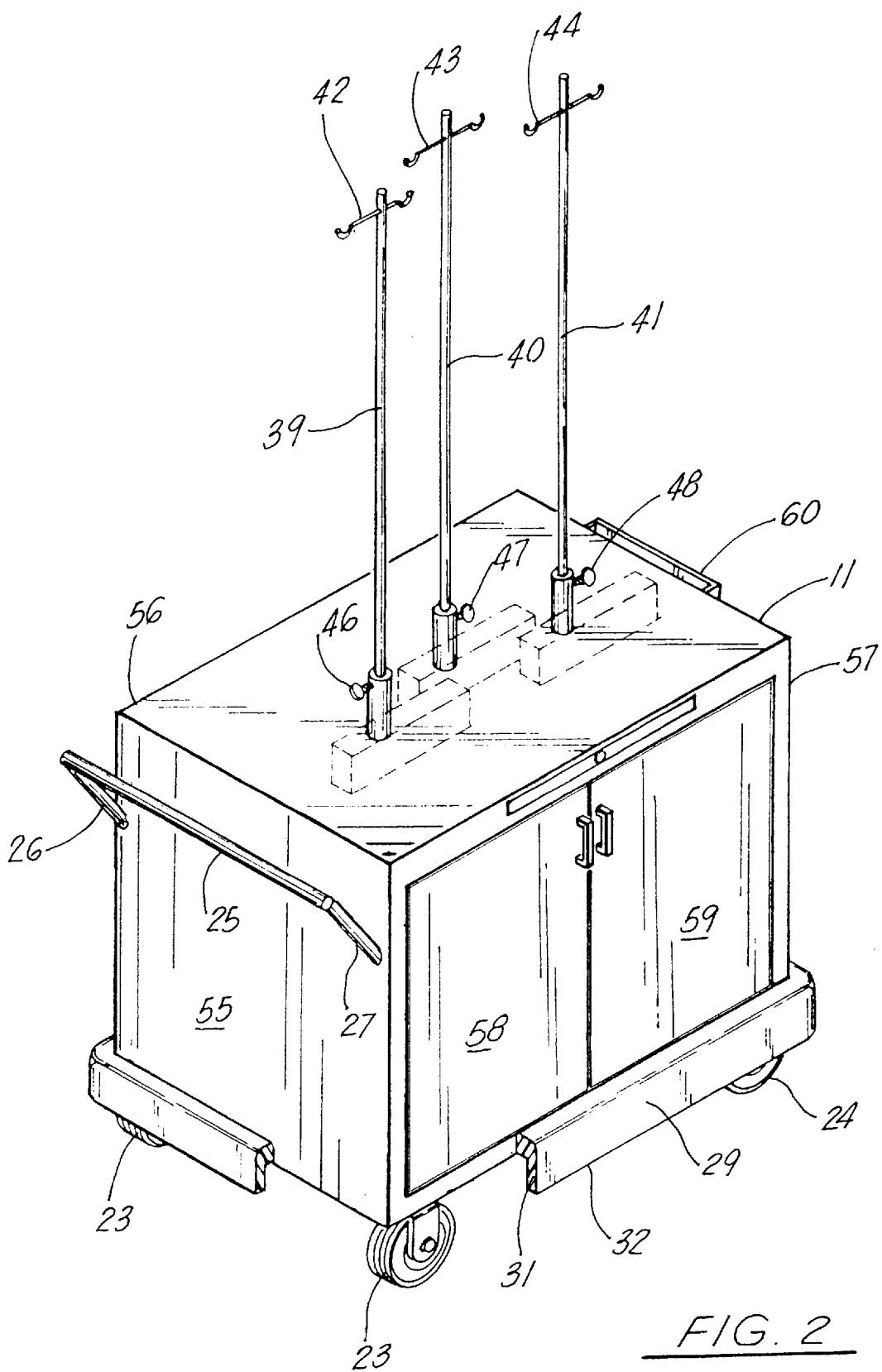
FIG. 2 is a perspective view of an alternative embodiment of the apparatus of the present invention

In FIG. 2, an alternate embodiment includes a frame 11 that has side walls 55–57 connecting between the upper plate 13 and lower plate 12. The side walls 55–57 in combination with doors 58, 59 define a cabinet that can hold articles therein, within a hollow interior.

Figure 4:
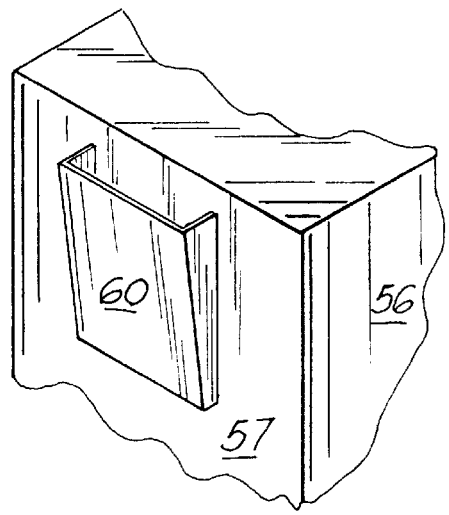
FIG. 4 is a fragmentary perspective view of the preferred embodiment of the apparatus of the present invention.

In FIG. 4, a side pocket 60 can be placed on the side wall of alternate embodiment for the purpose of carrying a patient's chart.

Figure 5:
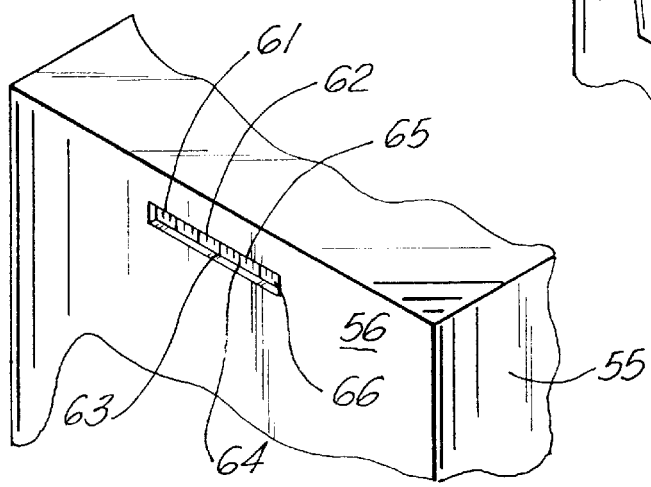
FIG. 5 is a fragmentary perspective view of the preferred embodiment of the apparatus of the present invention.
Figure 6:
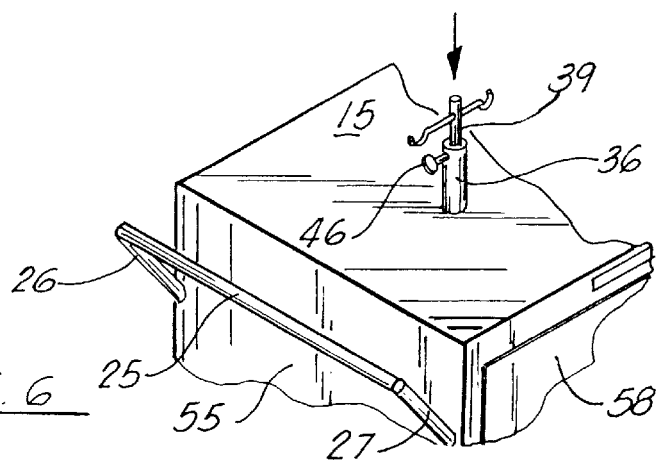
FIG. 6 is a fragmentary perspective view of the alternate embodiment of the apparatus of the present invention illustrating the telescoping rod in retractive position.

In FIG. 5, a plurality of electrical receptacles 61–66 are shown. The electrical receptacles 61–66 allow numerous medical instruments (e.g. IV pumps, patient's monitors and the like) to be plugged into an electrical supply source that communicates with the receptacles 61–66 via an extension cord.

The following table lists the parts numbers and parts description used herein and in the drawings attached hereto.

PARTS LIST

| Part Number | Description |
| --- | --- |
| 10 | fluids support cart |
| 10A | fluids support cart |
| 11 | frame |
| 12 | bottom plate |
| 13 | top plate |
| 14 | storage shelf |
| 15 | work surface |
| 16 | knob |
| 17 | opening |
| 18 | front panel |
| 19 | post |
| 20 | post |
| 21 | post |
| 22 | post |
| 23 | casters |
| 24 | casters |
| 25 | handle |
| 26 | diagonal member |
| 27 | diagonal member |
| 28 | horizontal member |
| 29 | skirt |
| 30 | horizontal section |
| 31 | vertical section |
| 32 | lower edge |
| 33 | telescoping pole |

PARTS LIST-continued

| Part Number | Description |
| --- | --- |
| 34 | telescoping pole |
| 35 | telescoping pole |
| 36 | outer tube |
| 37 | outer tube |
| 38 | outer tube |
| 39 | inner pole |
| 40 | inner pole |
| 41 | inner pole |
| 42 | hanger |
| 43 | hanger |
| 44 | hanger |
| 45 | hook |
| 46 | set screw |
| 47 | set screw |
| 48 | set screw |
| 49 | "X" axis |
| 50 | "Y" axis |
| 51 | plate side |
| 52 | plate side |
| 53 | plate side |
| 54 | plate side |
| 55 | side wall |
| 56 | side wall |
| 57 | side wall |
| 58 | door |
| 59 | door |
| 60 | side pocket |
| 61 | receptacle |
| 62 | receptacle |
| 63 | receptacle |
| 64 | receptacle |
| 65 | receptacle |
| 66 | receptacle |

Because many varying and different embodiments may be made within the scope of the inventive concept herein taught, and because many modifications may be made in the embodiments herein detailed in accordance with the descriptive requirement of the law, it is to be understood that the details herein are to be interpreted as illustrative and not in a limiting sense.

What is claimed as invention is:

1. A support cart for supporting intravenous fluid dispensing articles comprising:

a) a frame that includes a lower base with multiple corners and an upper table positioned above the base with a work surface thereon, the base and work surface each having generally rectangular periphery;

b) the table having X and Y axes that intersect the center of the table work surface and which respectively intersect parallel sides of the work surface;

c) a plurality of vertical intravenous fluid container support poles mounted on the frame and extending through the table, each supported pole being telescoping to adjust to multiple elevational positions, each support pole including a lower outer tube portion and an upper inner tube portion that telescopes within the outer tube portion, at least two of the poles being on one side of the Y axis and the other of the poles being on the other side of the Y axis, and at least two of the poles being on opposite sides of the X axis;

d) a plurality of casters positioned respectively at the corners of the lower base portion of the frame; and e) a movable table portion that is extendable from the upper table surface and substantially parallel thereto.

\* \* \* \* \*